United States Patent [19]

Kim

[11] Patent Number: 5,877,214
[45] Date of Patent: Mar. 2, 1999

[54] POLYARYL-POLY(ETHYLENE GLYCOL) SUPPORTS FOR SOLUTION-PHASE COMBINATORIAL SYNTHESIS

[75] Inventor: Ronald M. Kim, Monmouth Junction, N.J.

[73] Assignee: Merck & Co., Inc., Rahway, N.J.

[21] Appl. No.: 923,299

[22] Filed: Sep. 4, 1997

Related U.S. Application Data

[60] Provisional application No. 60/025,927 Sep. 12, 1996.
[51] Int. Cl.⁶ .................................................. A61K 31/19
[52] U.S. Cl. ......................... 514/571; 514/576; 514/650; 562/42; 562/426; 562/452; 562/470; 564/337; 564/346; 564/348; 564/355; 568/62; 568/609; 568/607
[58] Field of Search ............................. 562/42, 426, 452, 562/470; 508/62, 604, 607; 514/571, 576, 650; 564/331, 346, 348, 355

[56] References Cited

U.S. PATENT DOCUMENTS 5,041,516  8/1991  Frethet et al. .
5,338,532  8/1994  Tomalia et al. .
5,362,843  11/1994  Vicari et al. .

OTHER PUBLICATIONS

Gitsov, I., et al., *J. Am. Chem. Soc.*, 1996, 118, 3785–3786.

Han, H., et al., *Proc. Natl. Acad. Sci. USA*, 1995, 92, 6419–6423.

Han, H., et al., *J. Am. Chem. Soc.*, 1996, 118, 2539–2544.

Padias, A.B., et al., *J. Org. Chem.*, 1987, 52, 5305–5312.

Tomalia, et al., *Angew. Chem. Int. Ed. Engl.*, 1990, 29, 138–175.

*Primary Examiner*—Samuel Barts
*Attorney, Agent, or Firm*—J. Eric Thies; David L. Rose

[57] ABSTRACT

The present invention is directed to the certain polyaryl-poly(ethylene glycol) compounds ("polyaryl-PEG" compounds) which are useful as soluble polyvalent supports in the preparation of combinatorial libraries of compounds. The resultant combinatorial libraries are useful in screening for biologically active moieties in the drug discovery process or in developing compounds with desired physical and chemical properties.

20 Claims, No Drawings

POLYARYL-POLY(ETHYLENE GLYCOL) SUPPORTS FOR SOLUTION-PHASE COMBINATORIAL SYNTHESIS

CROSS REFERENCE TO RELATED APPLICATIONS

This application claims priorty under 35 U.S.C. § 119(e) from U.S. Ser. No. 60/025,927, filed Sep. 12, 1996.

BACKGROUND OF THE INVENTION

The standard method for searching for new chemical compounds which can effectively modulate biological processes employs the screening of pre-existing compounds in assays which have been designed to test particular properties of the compound being screened. Similarly, in designing compounds having desired physiochemical properties for general chemical applications, numerous compounds must be individually prepared and tested.

To reduce the time and expense involved in preparing and screening a large number of compounds for biological activity or for desirable physiochemical properties, technology has been developed for providing libraries of compounds for the discovery of lead compounds. Current methods for generating large numbers of molecularly diverse compounds focus on the use of solid phase synthesis. The generation of combinatorial libraries of chemical compounds by employing solid phase synthesis is well known in the art. For example, Geysen, et al. (*Proc. Natl. Acac. Sci. USA*, 3998 (1984) describe the construction of multi-amino acid peptide libraries; Houghton, et al. (*Nature*, 354, 84 (1991) and PCT Patent Pub. No. WO 92/09300) describe the generation and use of synthetic peptide conbinatorial libraries for basic research and drug discovery; Lam, et al. (*Nature*, 354, 82 (1991) and PCT Patent Pub. No. WO 92/00091) describe a method of synthesis of linear peptides on a solid support such as polystyrene or polyacrylamide resin.

The growing importance of combinatorial chemistry as an integral component of the drug discovery process has spurred extensive technological and synthetic advances in the field (Thompson, L. A.; Ellman, J. A. (1996) *Chem. Rev.* 96, 555–600). Founded in peptide synthesis devised by Merrifield, solid phase chemistry has emerged as the preeminent method for construction of small molecule combinatorial libraries (see e.g. Merrifield, R. B. (1963) *J. Am. Chem. Soc.* 85,2149–2154; (a) Terrett, N. K.; Gardner, M.; Gordon, D. W.; Kobylecki, R. J.; Steele, J. (1995) *Tetrahedron* 51(30), 8135–8173. (b) Gordon, E. M.; Barrett, R. W.; Dower, W. J.; Fodor, S. P. A.; Gallop, M. A. (1994) *J. Med. Chem.* 37, 1385–1401.).

It is known that a wide variety of organic reactions can be carried out on substrates immobilized on resins. These include, in addition to peptide synthesis, nucleophilic displacements on benzylic halides, halogenation, nitration, sulfonation, oxidation, hydrolysis, acid chloride formation, Friedel-Crafts reactions, reductions, metallation, and the like which are well known in the art. (See for example, Mathur, et al., "Polymers as Aids in Organic Chemistry", Academic Press, New York, 18 (1980) and Farrall, et al.,*J. Org. Chem.,* 41, 3877 (1976)).

One variant on the use of substrates imobilized on resin beads employs polystyrene pins as supports for the substrates (see Geysen, et al., *J. Immunol. Meth.,* 102, 259 (1987) and another variant employs a flat solid support in the form of a tape or a streamer (see PCT Patent Publication WO 96/16078, published May 30, 1996).

Although combinatorial chemistry may be attempted by employing traditional synthetic chemistry in the solution phase, this is essentially impractical due to the difficulty in separating complex mixtures of intermediates and final compounds from reagents and solvents. Traditional solution phase chemistry has been criticized as being unsuitable as a technique which aims to simultaneously produce a multiplicity of new products, since this would not allow physical separation among the different products. The products are therefore likely to be contaminated with excess reagents, by-products, etc., leading to difficulties in separation and purification.

Central to the power of solid phase synthesis is the ease by which reagents and solvents are removed simply by washing. This allows for the purification of resin-bound mixtures of great complexity, and the use of large reagent excesses to drive reactions to completion. The "infinite dilution" obtained on solid supports can also prevent side reactions which may occur in solution. Despite its advantages, nontrivial liabilities are associated with solid phase synthesis. Most notable is the often arduous task of modifying solution phase chemistry to the solid phase, with its potential pitfalls such as poor solvation, differential site accessibility, and incompatibility of the polymer support with reagents or reaction conditions. Often the most time-consuming aspect of combinatorial library synthesis is not construction of the library itself, but rather translation of solution phase chemistry to the solid phase. Although a significant portion of organic chemistry can be adapted to synthesis on the solid phase, some reactions, such as heterogeneous catalysis, would be exceedingly difficult to conduct on reagents linked to a solid phase support. In addition to synthetic complications which may arise from employing a solid support, few analytical techniques exist for characterization of resin-bound compounds. Even if NMR or IR analytical methods are attempted, they usually require specialized equipment and techniques and often yield spectra of low quality. Thus, it is very difficult to monitor reactions conducted on solid phase. Even analysis of cleaved intermediates can be ambiguous, since the harsh cleavage conditions that are often required may be detrimental to the molecules of interest.

Accordingly, alternative methodology for the preparation of combinatorial libraries which overcomes the drawbacks of solid phase synthesis would provide a significant advance in the field.

Classical solution phase techniques have been developed in an attempt to overcome the drawbacks of solid phase synthesis. One approach is to separate acidic and basic reagents from the resultant products by adding a water solution of additional acids or bases (See Boger, et al,*J. Am. Chem. Soc.*, (Feb. 28, 1996)). A variant of this method takes advantage of extraction of the reagents or products into a perfluorocarbon solvent.

Another approach, termed liquid-phase combinatorial synthesis (LPCS), in which combinatorial libraries are synthesized on soluble polyethylene glycol (PEG) supports has been recently described (Han, H.; Wolfe, M. M.; Brenner, S.; Janda, K. D. *Proc. Natl. Acad. Sci USA,* 92, 6419–6423 (1995) and Han, H.; Janda, K. D. *J. Am. Chem. Soc.,*118, 2539–2544 (1996)). In this method, monofunctional PEG which falls within a certain molecular weight range is used as a support for synthetic reactions. When the reactions are complete, ether is added to the solution which causes precipitation of the PEG, which is then isolated by filtration. This precipitation/crystallization of the PEG-protected molecules from ether allows for removal of reagents and solvents by filtration, thus combining the advantages of solution phase chemistry and the utility of solid phase purification. This technology has been reviewed in *Science*, 272, 1266–1268 (May 31, 1996).

Certain polyvalent poly(ethylene glycol) compounds have been disclosed, but they have not been previously noted as being useful as soluble supports for solution phase combinatorial chemistry (Padias, A. B.; Hall, H. K. Jr.; Tomalia, D. A.; McConnell, J. R. *J. Org. Chem.*, 52, 5305–5312 (1987); Gitsov, I.; Frechet, J. M. J. *J. Am. Chem. Soc.*, 118, 3785–3786 (1996)).

The use of a soluble polyvalent support in accordance with the present invention provides significant advantages with respect to solid phase synthesis of combinatorial libraries, including: (1) solution phase synthesis obviates the need to modify chemistry to the solid phase; (2) intermediates may be routinely characterized by a variety of analytical methods, including $^1$H and $^{13}$C NMR, IR, UV and mass spectrometry, with the generation of NMR spectra of generally high resolution being made possible; (3) because multiple copies of each molecule are synthesized per polyvalent support, extremely high loadings may be attained; (4) size-based purification is general, since it does not rely on other physical differences between support-bound compounds and reagents; the use of large reagent excesses are also permitted; and (5) polyvalent supports offer a flexible framework that may be engineered to exhibit properties necessary for their desired applications. Combinatorial chemistry on soluble polyvalent supports thus provides a valuable alternative to solid phase synthesis.

Commercially available Starburst™ polyamidoamine (PAMAM) dendrimers have been employed as a soluble support for combinatorial synthesis. However, PAMAM is not an ideal support for solution-phase chemistry, since the amine and amide moieties may be reactive under some conditions, and variable solubility of the dendrimers in organic solvents may limit the scope of chemistry which can be performed on the PAMAM supports. In addition, broad $^1$H NMR signals observed for the PAMAM species could hinder characterization of bound intermediates.

Accordingly, the present compounds provide several advantages over previously used PAMAM dendrimers which are important for their use as soluble supports for combinatorial chemistry, including: (1) greatly enhanced solubility in a range of solvents, which broadens the scope of chemistry that can be performed, (2) significantly sharper $^1$H NMR signals, which facilitates characterization of bound intermediates, and (3) higher chemical stability, which expands the scope of chemistry that can be carried out with such polyvalent supports.

SUMMARY OF THE INVENTION

The present invention is directed to certain polyaryl-poly(ethylene glycol) compounds which are useful as soluble polyvalent supports in the preparation of combinatorial libraries of compounds. These polyaryl-PEG compounds are comprised of polyaryl cores bearing poly(ethylene glycol) chains which are attached through alkyl spacers. Synthons can be attached directly to the poly(ethylene glycol) termini, or to chemical linkers covalently attached to the poly(ethylene glycol) chains. These soluble polyvalent supports are useful in the preparation of a combinatorial library by facilitatating the use of standard solution phase chemistry, and allowing homogeneous purification, routine characterization of intermediates, and high support loading.

The present invention is further directed to a combinatorial library of compounds wherein the combinatorial library contains such compounds as a soluble polyvalent support. The present invention further embraces a combinatorial library of compounds which comprises a plurality of compounds attached to these soluble polyvalent supports.

DETAILED DESCRIPTION OF THE INVENTION

The present invention is directed to a compound of the Formula I, II or III:

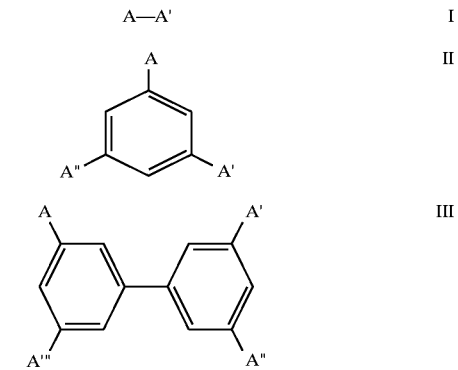

wherein:
A, A', A" and A'" are independently selected from:

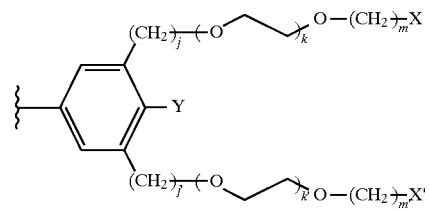

X and X' are independently selected from the group consisting of:
—OH, —Br, —Cl, —I, —SH, —CO$_2$H, —CO$_2$Cl, CO$_2$Br, —SO$_3$H, —SO$_2$Cl, —NH$_2$, and —CH=CH$_2$;
Y is independently selected from the group consisting of:
hydrogen, —CH$_3$, —O—(C$_{1-6}$alkyl) and —O(CH$_2$CH$_2$O)$_n$—CH$_3$;
j and j' are independently an integer from 0 to 4, inclusive;
k and k' are independently an integer from 1 to 12, inclusive;
m and m' are independently an integer from 1 to 4, inclusive; and
n is an integer from 0 to 12, inclusive;
and salts thereof.

Preferred compounds of the instant invention include those of Formula I, II and III wherein j and j' are 1, 2 or 3. Even more preferred compounds of the instant invention include those of Formula I, II and III wherein j and j' are 1 or 3.

Preferred compounds of the instant invention include those of Formula I, II and III wherein k and k' are 3 to 7, inclusive. Even more preferred compounds of the instant invention include those of Formula I, II and III wherein k and k' are 3, 4 or 5.

Preferred compounds of the instant invention include those of Formula I, II and III wherein m and m' are 2 or 3. Even more preferred compounds of the instant invention include those of Formula I, II and III wherein m and m' are 2.

Preferred compounds of the instant invention include those of Formula I, II and III wherein Y is independently selected from the group consisting of: hydrogen, —CH₃, and —OCH₃.

Preferred compounds of the instant invention include those of Formula I, II and III wherein X and X' are independently selected from the group consisting of: —OH, —Br, —NH₂, and —CO₂H. Even more preferred compounds of the instant invention include those of Formula I, II and III wherein X and X' are —OH.

Preferred compounds of the instant invention include those of Formula I, II and III wherein Y is independently selected from the group consisting of: hydrogen, and —OCH₃.

In the compounds of Formula I, II and III, it is preferred that A, A', A" and A'" (if present in the compound of Formula I, II and III) are identical to each other, i.e. it is preferred that the compounds are symmetrical.

Preferred compounds of the instant invention include:

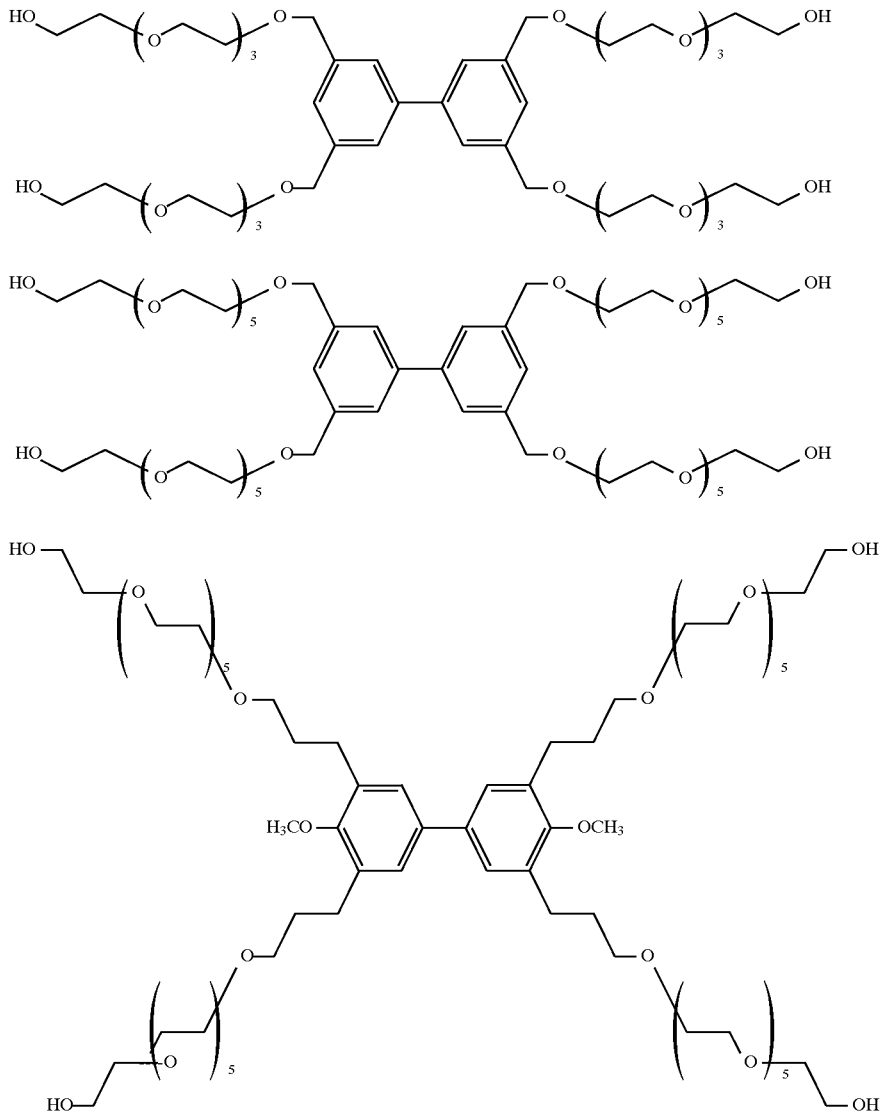

-continued

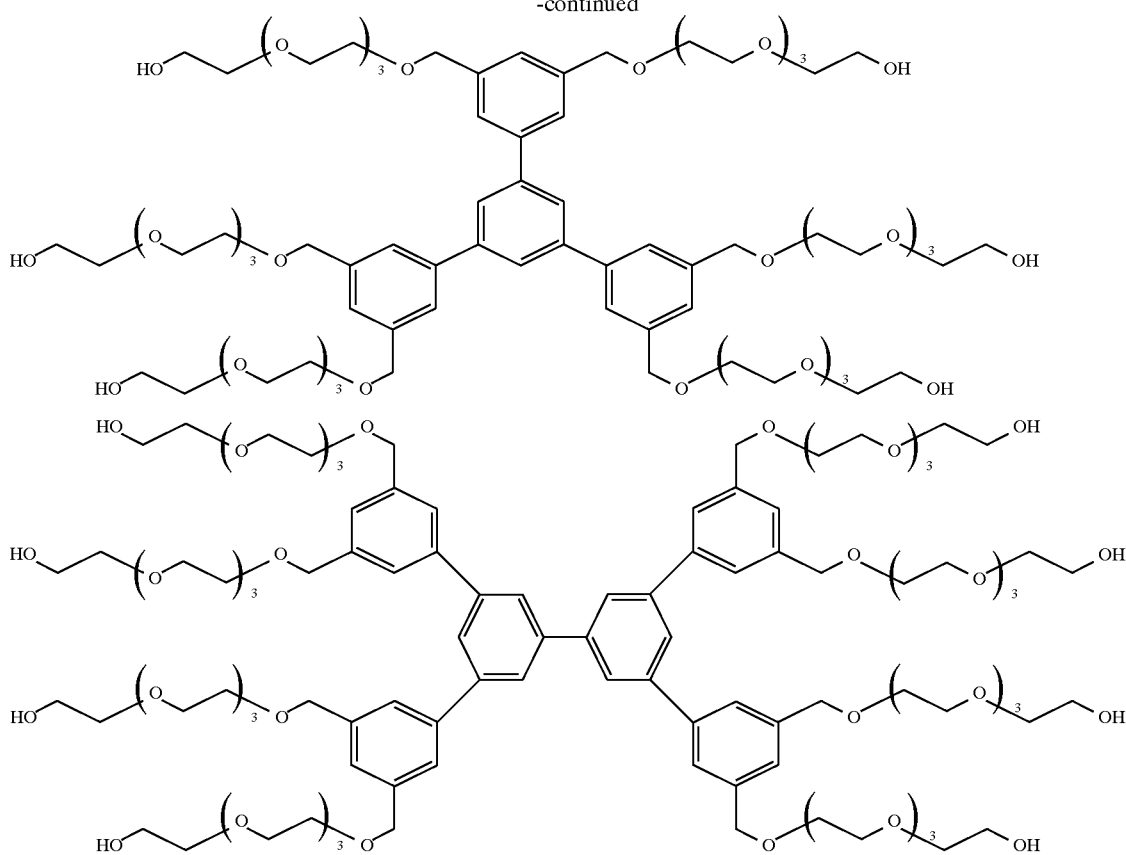

As will be appreciated by those skilled in the art, the compounds of Formula I are biphenyl compounds, the compounds of Formula II are 1,3,5-triphenylbenzene compounds, and the compounds of Formula III are 3,5,3', 5'-tetraphenylbiphenyl compounds.

The present invention envisions the use further modification of the present soluble polyvalent supports to facilitate manipulation and/or identification. Accordingly, the present invention is further directed to compounds wherein the compound of Formula I, II or III is covalently attached to a handle or linker functionality which facilitates the manipulation of the support or which acts as an anchor to facilitate the attachment/detachment of compounds thereto. Such handles or linkers include those which are known for use in solid phase synthesis, including 2,4-dimethoxy-4'-hydroxybenzophenone, 4-(4-hydroxymethyl-3-methoxyphenoxy)-butryic acid (HMPBA), 4-hydroxymethylbenzoic acid, 4-hydroxymethyl-phenoxyacetic acid, 3-(4-hydroxymethylphenoxy)-propionic acid, p-[(R,S)-α-[1-(9H-fluoren-9-yl)methoxyformamido]-2,4-dimethoxybenzyll]-phenoxyacetic acid, p-chloromethylphenyl linker, p-hydroxymethylphenyl linker, MBHA linker, HMBA-MBHA linker, Wang linker, Nova Syn TGA linker, Rink acid linker, Rink amide linker, Rink amide MBHA linker, Sieber liker, trityl linker, and the like.

In addition, the present invention is further directed to compounds wherein the compound of Formula I, II or III is attached to functionality which acts as a label or tag to facilitate the identification or characterization of the support (and any compounds attached thereto). Such labels or tags include chemical or radiochemical moieties which are capable of being distinguished from other chemical moieties and which are capable of being detected at low levels (such as at $10^{-18}$ to $10^{-19}$ mole), such as fluorescent labels. Representative tags include those disclosed in PCT Patent Publications WO 95/16209, WO 95/28640, WO 97/14814 and WO 97/15390.

The present invention is also directed to a method for the use of the instant compounds in the preparation of a combinatorial library.

The present invention is further directed to a combinatorial library wherein the combinatorial library is prepared by employing a compound of Formula I, II or III.

Accordingly, the present invention further embraces a combinatorial library which comprises a plurality of compounds attached to a compound of Formula I, II or III.

The present invention further embraces a combinatorial library wherein the combinatorial library is prepared by employing a compound of Formula I, II or III.

The present invention is further directed to a kit for combinatorial synthesis which comprises a compound of Formula I, II or III.

In an embodiment of the present invention the instant polyaryl-poly(ethylene glycol) soluble supports may be used for the preparation of combinatorial libraries. In a preferred embodiment the present invention is directed to a process for the preparation of combinatorial libraries which comprises: (1) attaching a first synthon to a soluble polyvalent support to form a support-bound synthon; (2) separating the support-bound synthon from the reaction media; (3) optionally, mixing the support-bound synthon with one or more different support-bound synthons; (4) reacting the support-bound synthon or mixture of support-bound synthons with another synthon to form a support-bound product or mixture of support-bound products; (5) separating the support-bound product or mixture of support-bound products from the reaction media. In the above process, the order of steps (2) and (3) may be interchanged. In the above process, steps (3)–(5) may be repeated multiple times to afford the desired product or products. Optionally, the support-bound product or mixture of support-bound products may be cleaved and isolated from the support.

In a preferred embodiment, the present invention is directed to such a process which is conducted by automation or under computer control, since both the synthesis and purification steps are performed in solution.

By the term "polyvalent support" is meant a compound of Formula I, II or III.

By the term "soluble" is meant that the polyvalent support is dissolved in the appropriate solvent selected for the reaction media or subsequent manipulations. If desired, the polyvalent support may be soluble in the reaction media and insoluble in the solvents employed in a subsequent manipulation to facilitate isolation of the support by e.g. precipitation.

By the term "synthon" is meant any chemical moiety which may be synthetically manipulated to permit its covalent linking to a support or to another synthon. To facilitate the separation of the synthon from the polyvalent support it is preferred that the synthon be attached via a chemically cleavable linker. Upon cleavage from the support, the linked synthons comprise discrete molecular entities which may be analyzed for their biological activity or physiochemical properties, or which may be subjected to further chemical modification.

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. Such salts are useful for convenience in synthesis or for in isolating or purifying the product.

The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

In the present invention, the polyvalent support may be separated from solvents and reagents or otherwise purified by methods known in the art including, crystallization, precipitation, ultrafiltration, gel permeation chromatography (GPC) (i.e. size exclusion chromatography (SEC)), precipitation, centrifugation, dialysis or selective adsorption. Preferred methods include ultrafiltration, size exclusion chromatography, precipitation, centrifugation and selective adsorption, in which the most preferred methods include ultrafiltration, size-exclusion chromatography and precipitation.

The extremely high loadings capable on a polyvalent support greatly facilitates the production of multimilligram quantities of compounds. The ability to achieve high support loading increases efficiency by diminishing the physical size of the reactor which is required for the preparation of useful amounts of the desired compounds.

A combinatorial library is a collection of compounds in which the compounds comprising the collection are composed of one or more subunits or monomeric units (i.e. synthons). The subunits may be selected form natural or unnatural moieties including amino acids, nucleotides, sugars, lipids, carbohydrates, dienes, dienopholes, and the like. The compounds of the combinatorial library differ in one or more ways with respect to the type(s), number, order or modification of the subunits comprising the compounds.

The combinatorial libraries generated by the methods of the present invention may be screened for pharmacologically or diagnostically useful compounds, as well as for desired physical or chemical properties. It will be clear to one skilled in the art that such screening may be conducted on a library of compounds which have been separated from the polyvalent support, or may be conducted directly on the library of compounds which are still linked to the polyvalent support.

The present invention provides a general method by which any variety of single compounds or libraries may be created. Furthermore, polyvalent supports present a modular framework which can be custom-tailored so as to be applicable to a variety of synthetic methodologies.

The present invention is useful for developing new drugs and chemical entities. The invention is useful for rapidly generating and systematically synthesizing large numbers of molecules that may vary in their chemical structure or composition. The invention is further useful for randomnly generating a large number of candidate compounds, then later optimizing those compounds which exhibit the most desirable properties.

As will be readily apparent to one skilled in the art, the present invention has application in essentially any synthetic reaction which may be conducted in the solution phase. Thus, the present invention is useful in almost all of the synthetic reactions which are known to one of skill in the art, including peptide synthesis, acylation, alkylation, condensation, cyclization, halogenation, heterogeneous catalysis, hydrolysis, metallation, nitration, nucleophilic displacement, organometallic reactions, oxidation, reduction, sulfonation, acid chloride formation, Diels-Alder reaction, Friedel-Crafts reactions, Fischer indole synthesis, Michael reactions, and the like (see e.g., H. O. House, "Modern Synthetic Reactions", 2nd ed. (Benjamin/Cummings, Menlo Park 1972); J. March, "Advanced Organic Chemistry", 3rd ed., (John Wiley & Sons, New York, 1985); Fieser and Fieser, "Reagents for Organic Synthesis", Volumes 1-end (Wiley Interscience, New York)). Likewise, the present invention has application in essentially any synthetic reaction which may be conducted on solid phase supports, including acetal formation, alkylations, alkynation, chiral alkylation, reductive alkylation, carbanion reactions, grignard reactions, ortanocadmium/manganese reactions, organolithim reactions, organozinc reactions, carbene insertion, condensations, Claisen reactions, aldol reactions, Dieckmann cyclization, Knoevenagel condensations, mannich reactions, cycloadditions, cyclizations (in particular to form heterocyclic rings), Friedel-Crafts reactions, halogenation, bromination, chlorination, nucleophilic addition, Michael addition, aromatic nucleophilic substitution, Finkelstein reaction, Mitsunobu reaction, palladium (0) catalyzed reactions, Stille coupling, Suzuki coupling, Heck reaction, carbamate/urea formation, oxidation of primary alcohol to aldehyde, Sharpless reaction, oxidation of secondary alcohol to ketone, oxidation of aldehyde to carboxylic acid, epoxidation, oxidation of primary chloride to aldehyde, oxidative phenol coupling, reduction of acid to alcohol, reduction of aldehyde to alcohol, reduction of alkyne to alkene, reduction of amide to amine, reduction of aryl nitro to amine, reduction of azide to amine, reduction of ester to alcohol, reduction of imine to amine, reduction of iodide to alkyl, reduction of ketone to alcohol, Wittig reaction, Horner-Emmons condensation, and the like (see generally, "Solid Phase Organic Chemistry (SPOC)" and "Solid Phase Inorganic Chemistry (SPIC)", Chiron Mimotopes, pp. 1–31 (August 1995).

As outlined schematically in Scheme 1, the present compounds may be employed as a soluble polyvalent support analogously to a solid phase support in traditional combinatorial synthesis, except that reactions are performed in solution, and intermediates bound to the polyvalent supports are separated by methods such as ultrafiltration, size exclusion chromatography, precipitation, centrifugation, dialysis or selective adsorption, and especially size-selective methods such as gel permeation chromatography or ultrafiltration. As will be clear to one skilled in the art, the steps may be repeated iteratively to incorporate additional synthons ($R^3$, $R^4$, etc) into the target compound (i.e. $R^1$—$R^2$—$R^3$—$R^4$, . . . etc.).

SCHEME 1

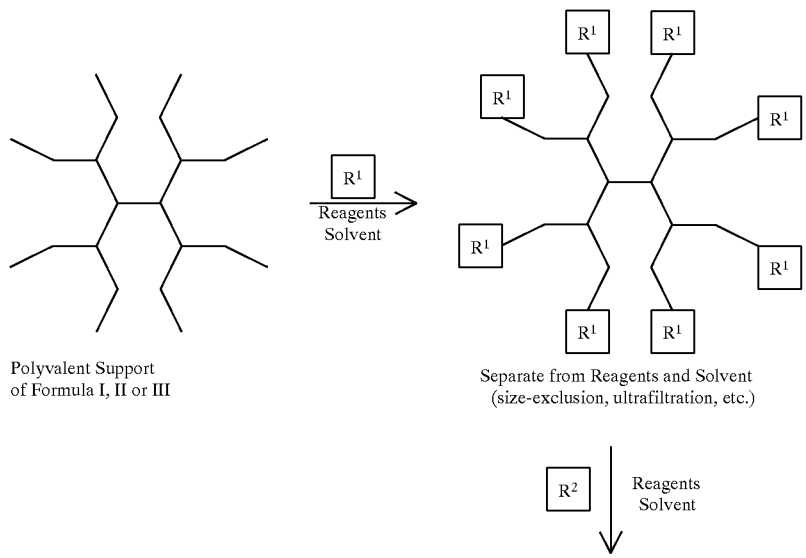

-continued
SCHEME 1

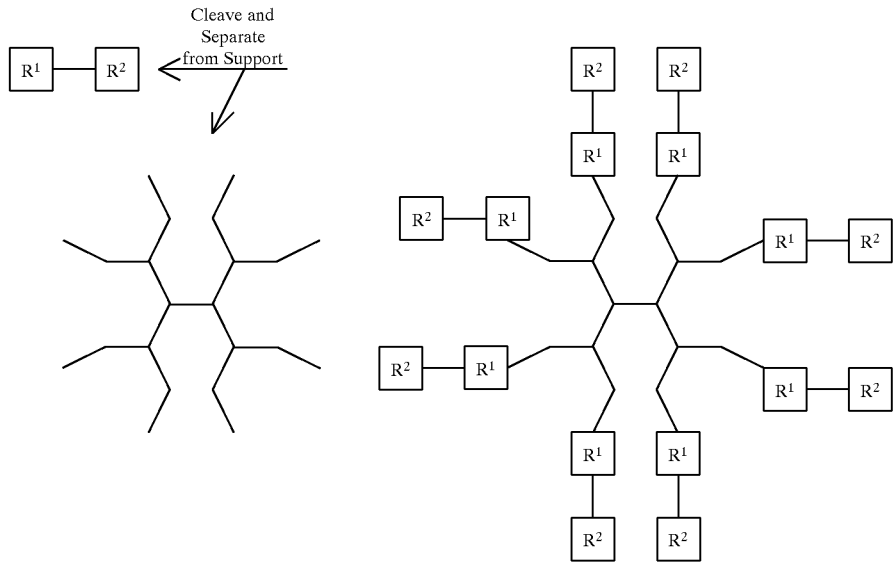

Separate from Reagents and Solvent
(optionally repeat to attach additional
synthons ($R^3$, $R^4$, etc.))

As used above, the generic depiction of a polyvalent support

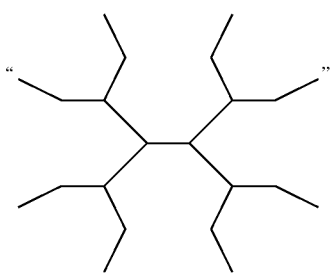

is not intended to represent any specific arrangement of carbon atoms, but is merely a graphical representation of the compound of Formula I, II or III which representation is employed for convenience and to facilitate ready comprehension of the essential features of the present invention.

The preparation of compounds of Formula I, II and III of the present invention may be carried out in sequential or convergent synthetic routes. Syntheses detailing the preparation of the compounds of Formula I, II and III in a sequential manner are presented in the following reaction schemes.

The general preparation of compounds of the present invention is described in the following Reaction Schemes.

Polyaryl-PEG supports may be prepared by either convergent or divergent schemes. A general convergent approach toward polyaryl-PEG production involves: (1) attachment of unprotected or monoprotected PEG chains to an aryl bromide or iodide, (2) conversion of the aryl halide to an aryl species capable of undergoing cross-coupling to an aryl halide (i.e. an aryl stannane or aryl boronic acid), (3) cross coupling of the aryl species with an aryl halide to form the polyaryl-PEG compound, and, if necessary, (4) deprotection of the PEG chains to afford the polyaryl-PEG support.

Specific examples of convergent schemes are detailed in the following examples. Alternatively, divergent schemes involving attachment of PEG chains to preformed polyaryl cores may also be used to prepared the instant polyaryl-PEG supports.

Asymmetric polyaryl-PEG supports may also be prepared. The chains on a given A may be differentiated by stepwise coupling of the aryl group with a single PEG chain (k, m, X), followed by coupling of a second chain (k', m', X'). X-groups may also be differentiated after attachment of the PEG chains to the aryl moiety by conversion of one of the X groups to X' (with employment of protecting groups as required). Polyaryl-PEG supports composed of different A-groups may also be prepared. One approach is to couple asymmetric aryl compounds to afford the asymmetric polyaryl species. For example, coupling of A-SnMe$_3$ with A'-Br yields asymmetric biphenyl A-A', while stepwise coupling of A-SnMe$_3$, A'-SnMe$_3$ and A"-SnMe$_3$ with 1,3,5-tribromobenzene yields the asymmetric triarylbenzene. Differences in reactivity of aryl species toward cross-coupling reactions (for example, the greater propensity of aryl iodides to undergo Stille cross-coupling reactions vs. aryl bromides) may also be exploited in the stepwise production of asymmetric polyaryl-PEG supports of types II and III. Asymmetry may also be conferred to the polyaryl-PEG supports by introduction of different PEG chains to a polyaryl core. This process would be facilitated by differentiating sites of PEG attachment on the polyaryl core (i.e. by employing benzyl bromide vs. benzyl chloride groups).

SCHEME 2

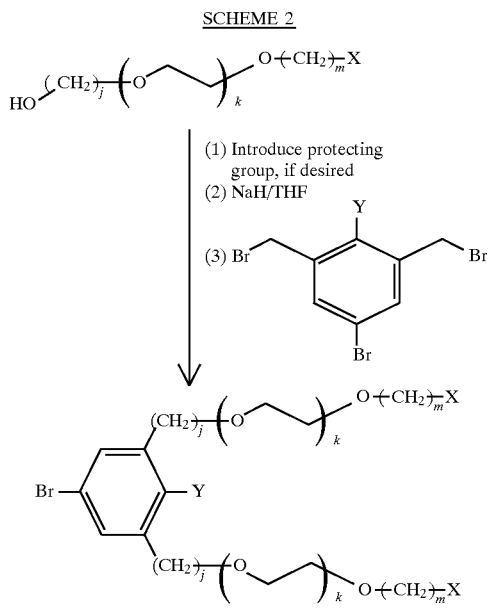

As outlined in Scheme 2, a polyethylene glycol bearing the desired functionality at X may be protected with an appropriate protecting group (if desired), then coupled with 3,5-bis-bromomethylbromobenzene to give the 3,5-bis (PEG)bromobenzene compound. If unsymmetrical compounds are desired (i.e. of the formula j', k', m' and X'), 3-bromomethyl-5-iodomethylbromobenzene may be reacted first with one polyethylene glycol, followed by reaction with a different polyethylene glycol. Due to the sensitive nature of the functionality at X, the use of protecting groups will generally be necessary. Alternatively, the desired functionality at X may be introduced at a later stage by synthetic modification of an appropriate polyaryl precursor.

SCHEME 3

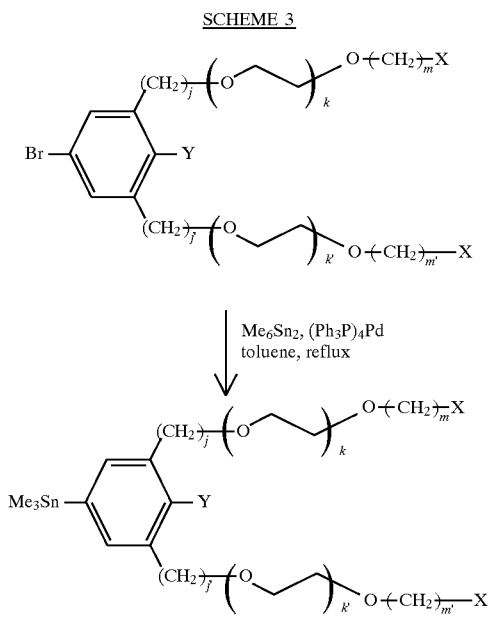

As outlined in Scheme 3, the aryl bromide is converted to the aryl stannane using hexamethylditin and catalytic tetrakis(triphenylphosphine)palladium(0) in refluxing toluene.

SCHEME 4

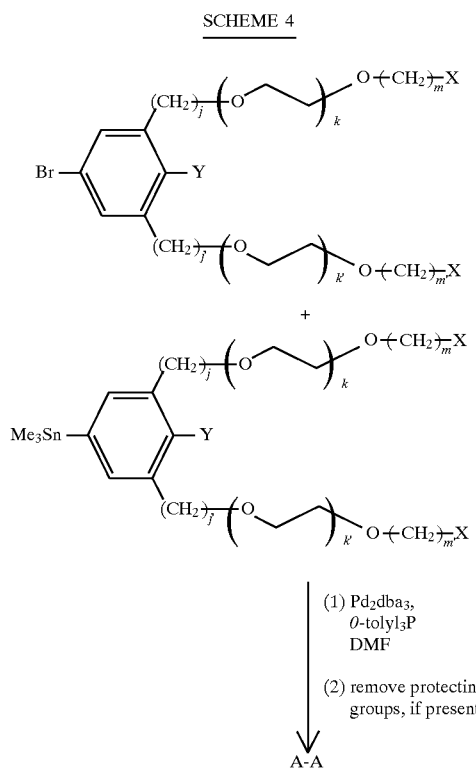

As outlined in Scheme 4, Pd-catalyzed Stille cross-coupling (or alternatively Suzuki coupling) of the aryl stannane with its precursor aryl bromide (and removal of protecting groups if present) to give the desired biphenyl compound. As will be readily apparent to one skilled in the art, the biphenyl compound may be symmetrical or unsymmetrical. Unsymmetrical biphenyl compounds may be prepared by reacting the aryl stannane with an aryl bromide which bears different substitutents.

SCHEME 5

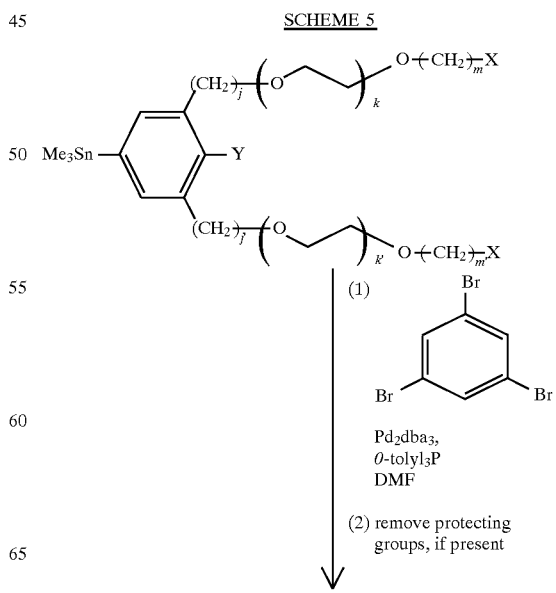

-continued
SCHEME 5

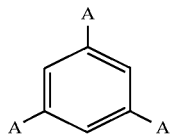

As outlined in Scheme 5, Pd-catalyzed Stille cross-coupling of the aryl stannane with 1,3,5-tri-bromobenzene (and removal of protecting groups if present) gives the desired 1,3,5-triaryl benzene compound. As will be readily apparent to one skilled in the art, the 1,3,5-triphenylbenzene compound may be symmetrical or unsymmetrical (i.e. bearing A, A', A"). Unsymmetrical 1,3,5-triphenylbenzene compounds may be prepared by reacting the phenyl tin derivative with a halo benzene (e.g. 1-iodo-3,5-dibromobenzene) followed by reaction with a different phenyl tin derivative.

SCHEME 6

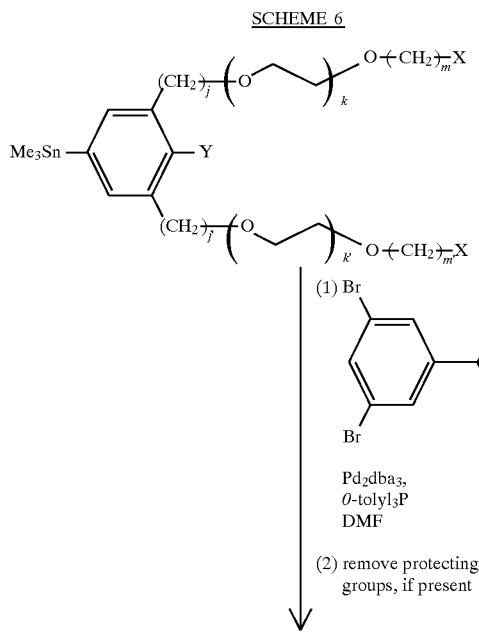

-continued
SCHEME 6

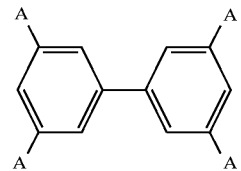

As outlined in Scheme 6, Pd-catalyzed Stille cross-coupling of the aryl stannane with 3,5,3',5'-tetrabromobiphenyl (and removal of protecting groups if present) gives the desired 3,5,3',5'-tetraarylbiphenyl compound. As will be readily apparent to one skilled in the art, the 3,5,3',5'-tetraphenylbiphenyl compound may be symmetrical or unsymmetrical (i.e. bearing A, A', A", A'").

The preparation of specific compounds of the present invention is depicted in Reaction Schemes 7 and 8.

SCHEME 7

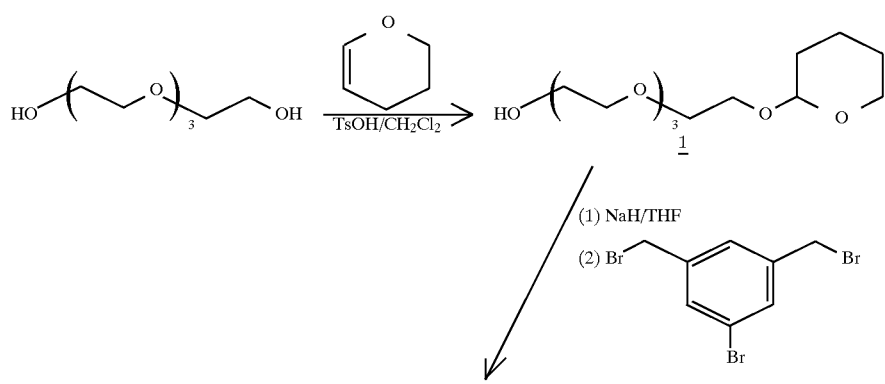

-continued
SCHEME 7

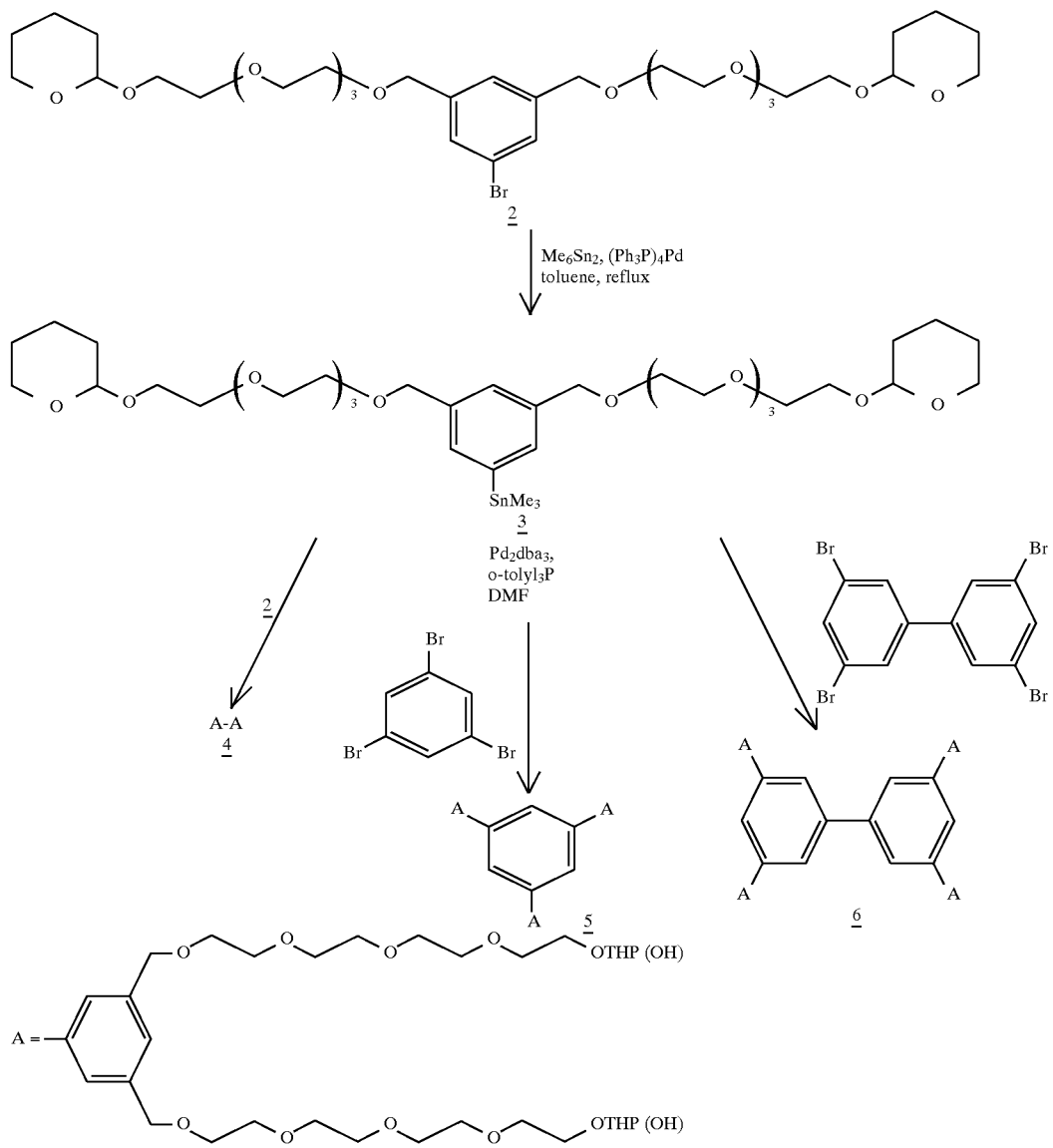

As depicted in Scheme 7, a convergent approach was used to prepare polyaryl-PEG supports of Formula I and II where j=1, k=3, m=2 and X=—OH (or —OTHP). Mono-THP protection of tetraethylene glycol, conversion to the sodium derivative and coupling with 3,5-bis-bromomethylbromobenzene afforded aryl bromide 2 bearing two PEG chains. Aryl bromide 2 was converted to the aryl stannane 3 using hexamethylditin and catalytic tetrakis(triphenylphosphine)palladium(0) in refluxing toluene. Pd-catalyzed Stille cross-coupling of 3 with either its precursor aryl bromide 2 or with 1,3,5-tribromobenzene or with 3,5,3',5'-tetrabromobiphenyl afforded the biphenyl species 4, the triaryl benzene compound 5, or the tetra aryl biphenyl compound 6, respectively. The deprotedtion of the THP-protected compounds is effected with MeOH containing catalytic toluenesulfonic acid to afford the corresponding alcohol.

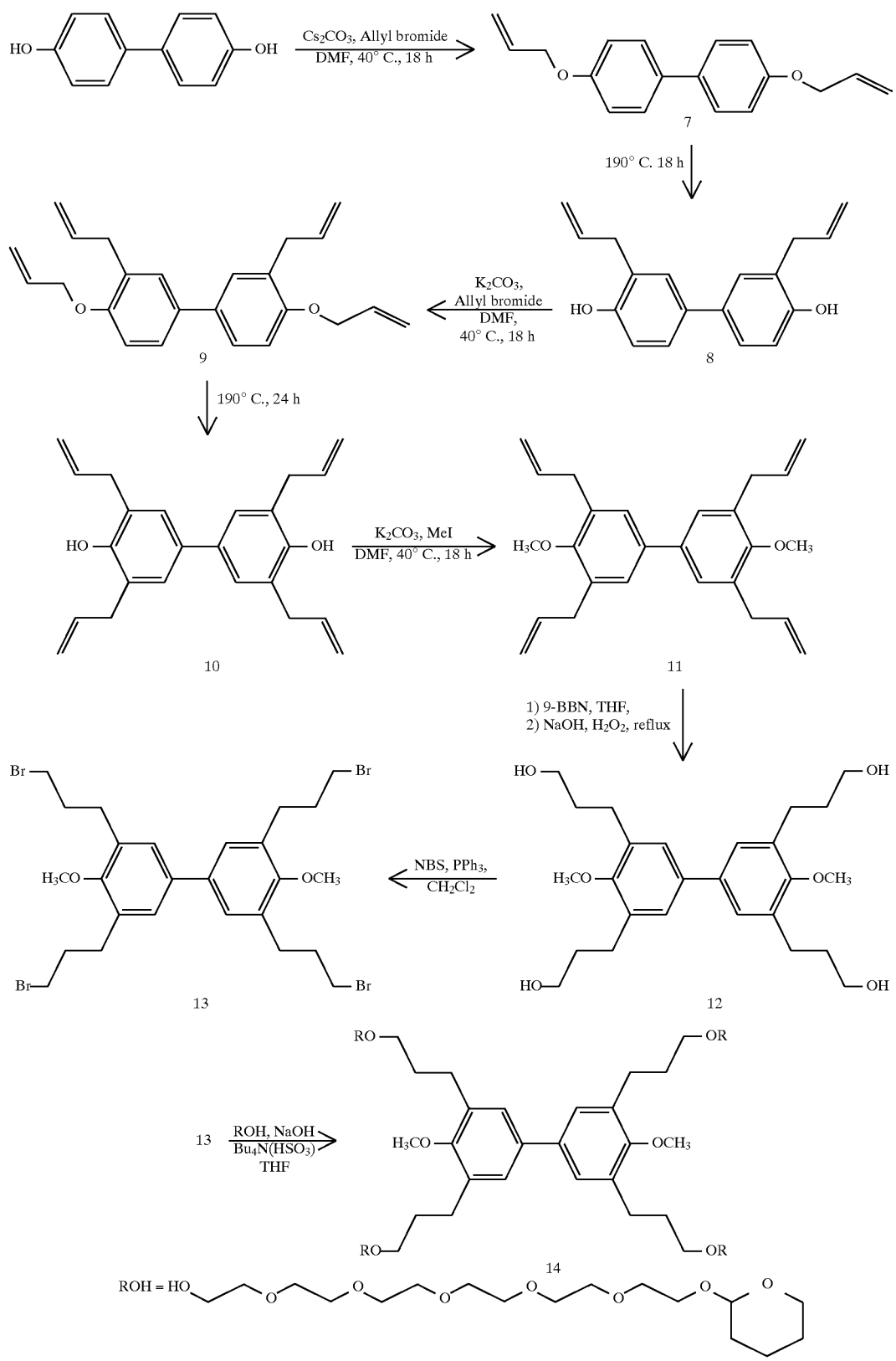
SCHEME 8

As depicted in Scheme 8, a sequential approach is used to prepare polyaryl-PEG supports of Formula I where j=3, k=5, m=2, Y=—OCH$_3$ and X=—OH (or —OTHP). Alkylation of 4,4'-biphenol with allybromide in DMF containing Cs$_2$CO$_3$ afforded allyl ether 7, which was converted to 3,3'-bis-allyl-4,4'-biphenol 8 by heating neat at 190° C. for 18 h. under nitrogen. Analogous re-allylation of biphenol 8, followed by Claisen rearrangement, yielded tetraallyl compound 10. Alkylation of 10 with MeI in presence of K$_2$CO$_3$ in DMF at 40° C. yielded dimethoxy species 11. Treatment of the tetraolefin with 9-BBN in THF, followed by hydrogen peroxide oxidation afforded tetra-ol 12, which was converted to tetrabromide 13 using NBS and PPh$_3$ in CH$_2$Cl$_2$. Formation of protected support 14 was achieved by nucleophilic displacement of the tetrabromide with mono-THP protected hexa(ethylene glycol) using NaOH in THF in presence of a phase-transfer catalyst. The deprotedtion of the THP-protected compounds is effected with MeOH containing catalytic toluenesulfonic acid to afford the corresponding alcohol.

Many of the starting materials are either commercially available or known in the literature and others can be prepared following literature methods described for analogous compounds. The skills required in carrying out the reaction and purification of the resulting reaction products are known to those in the art. Purification procedures include crystallization, ultrafiltration, size exclusion chromatography (gel permeation chromatography), precipitation, centrifugation, dialysis, selective adsorption, chromatography on silica gel (including flash chromatography), and normal phase or reverse phase chromatography.

As will be appreciated by one skilled in the art, protecting groups may be employed as required. The term "protecting group" is intended to indicate the presence of an appropriate protecting group, such as those described in Greene, T. W., Wuts, P. G. M. "Protective Groups in Organic Synthesis", 2nd ed., John Wiley & Sons, Inc., New York, 1991. An appropriate protecting group will be able to withstand the reaction conditions of intermediate processes, prior to being removed when desired. Suitable protecting groups for hydroxyl include those groups well known in the art such as: tetrahydropyranyl; 1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyldiphenylsilyl, ethyl-diphenylsilyl, propyl-diphenylsilyl, t-butyldiphenylsilyl, etc.), and the like; acyl such as aliphatic acyl, aromatic acyl and aliphatic acyl substituted with aromatic group, which are derived from carboxylic acids; and the like. Suitable protecting groups for amino include those groups well known in the art such as: benzyl, benzyloxymethyl, benzyloxycarbonyl (carbobenzyloxy), benzylsulfonyl, 2-bromoethyloxycarbonyl, t-butoxycarbonyl, 2-chlorobenzyloxycarbonyl, 2-chloroethyloxycarbonyl, di-t-amyloxycarbonyl, 9-fluoroenylmethyloxycarbonyl, isopropoxycarbonyl, 4-methoxybenzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, tirphenylmethane, and vinyloxycarbonyl groups, and the like. Methodology for the introduction and removal of protecting groups is well known in the art (see e.g. Greene, T. W., Wuts, P. G. M. "Protective Groups in Organic Synthesis", 2nd ed., John Wiley & Sons, Inc., New York, 1991).

The following examples are provided for the purpose of further illustration only and are not intended to be limitations on the disclosed invention.

EXAMPLES

Unless otherwise noted, all chemicals and reagents were purchased from commercial sources and used without further purification. Dimethylformamide (DMF) was dried over 3 Å and 13× sieves. Dimethylacetamide (DMA) was dried over 3 Å sieves. Gel permeation chromatography (GPC) was performed on a 2.5×30 cm column using Sephadex® LH-20 as the stationary phase and DMF as the eluent (flow rate=5 mL/min). $^1$H and $^{13}$C NMR were recorded at 500 MHz on a Varian Unity 500 spectrometer. HPLC spectra were obtained on a Hewlett Packard 1090 HPLC,equiped with a reverse-phase 100×2.1 mm Hewlett-Packard ODS (5 mm) Hypersil column. A linear elution gradient was employed, consisting of 9:1 H$_2$O/MeCN (0.1% TFA) brought to 100% MeCN (0.1% TFA) over 17 min, at a constant flow rate of 0.7 mL/min. Mass spectral data were recorded using a Finnigan MAT TSQ 700 (San Jose, Calif.) triple-stage quadrupole mass spectrometer. Samples were introduced into the mass spectrometer using an ABI 130 syringe pump HPLC equipped with a Brownlee 2.1×30 mm C-4 reverse-phase HPLC column. After injection, samples were eluted directly into the mass spectrometer using a linear gradient of acetonitrile. Spectra were recorded as describe by Griffin, P. R., Coffman, J. A., Hood, L. E., and Yates, J. R., III (1991) *Int. J. Mass Spectrom. Ion Processes*, 111, 131–149.

Example 1

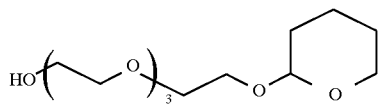

Tetraethylene glycol mono-tetrahydropyran-2-yl ether (1)

To a 20 mL solution of methylene chloride containing tetraethylene glycol (15 mmol, 2.91 g) and toluenesulfonic acid (20 mg) was added dropwise via syringe 3,4-dihydro-2H-pyran (12 mmol, 1.0 g, 1.1 mL). The reaction mixture was stirred for 3.5 h, and the solvent was removed by rotary evaporation. Mono-tetrahydropyran 1 was isolated by flash chromatography on silica eluting with 1:1 tetrahydrofuran/methylene chloride, affording 1.82 g of a clear, colorless oil (44% yield). $^1$H NMR (400 MHz, CDCl$_3$): δ4.61 (dd, 1H, J$_1$=J$_2$=4 Hz), 4.6–4.8 (m, 2H), 3.69 (t, 2H, J=7 Hz).

Example 2

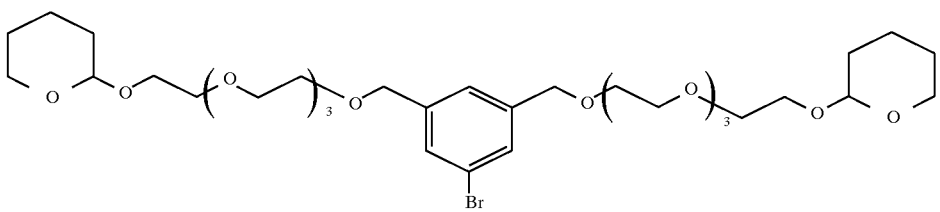

3,5-Bis-([tetrahydropyran-2-yl]tetraethylene glycoxymethyl)-bromobenzene (2)

To 5 mL of THF charged with NaH (6 mmol, 240 mg of a 60% slurry in mineral oil) was added dropwise under nitrogen a solution of 1 (6 mmol, 1.67 g) dissolved in 4 mL of THF. The solution was stirred at ambient temperature for 45 min, after which time 3,5-bis-bromomethylbromobenzene (2 mmol, 686 mg) dissolved in 3 mL of THF was added dropwise at a rate to allow gentle refluxing of the reaction. The reaction was stirred for 6 h at ambient temperature, after which time 50 mL of $H_2O$ was added. The resulting solution was extracted with 3×50 mL of $CH_2Cl_2$ and 2×50 mL of ethyl acetate. The combined organic phase was dried with $Na_2SO_4$, filtered, and the solvent was removed by rotary evaporation. The brown residue was purified by flash chromatography on silica eluting with 20% THF/$CH_2Cl_2$, affording 1.2 g of 2 as a clear oil (84% yield). $^1$H NMR (400 MHz, $CDCl_3$): δ7.40 (s, 2H), 7.18 (s, 1H), 4.61 (dd, 2H, $J_1=J_2=4$ Hz), 4.50 (s, 4H).

Example 3

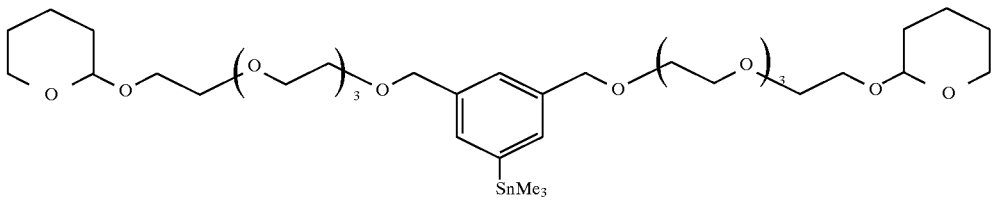

Dimethyl-(3,5-bis-[(tetrahydropyran-2-yl) tetraethylene glycoxymethyl]-phenyl)stannane (3)

To a solution of aryl bromide 2 (1 mmol, 738 mg) dissolved in 15 mL of toluene was added dropwise under $N_2$ hexamethylditin (1.2 mmol, 393 mg, 240 μL). After stirring the reaction mixture for 5 min, tetrakis(triphenylphosphine) palladium(0) (0.07 mmol, 80 mg) and triphenylphosphine (0.05 mmol, 13 mg) were added. The reaction mixture, which turned dark blue-black after several minutes, was refluxed under $N_2$ for 2 h, allowed to cool to ambient temperature and stirred overnight. The reaction mixture was filtered, and the solvent was removed by rotary evaporation. Purification of the crude product by flash chromatography on silica eluting with 1:20:79 MeOH/THF/$CH_2Cl_2$, afforded 698 mg of 3 as a yellow oil (85% yield). $^1$H NMR (400 MHz, $CDCl_3$): δ7.35 (d, 2H, J=2 Hz), 7.22 (t, 1H, J=2 Hz), 4.61 (dd, 2H, $J_1=J_2=4$ Hz), 4.50 (s, 4H).

Example 4

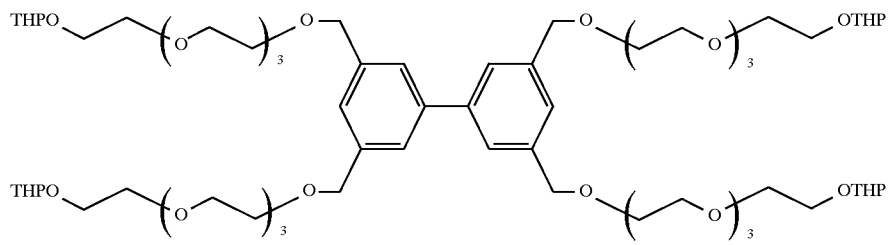

3,5,3',5'-Tetra-([tetrahydropyran-2-yl]tetraethylene glycoxymethyl)-biphenyl (4)

To a 10 mL solution of dry DMF containing aryl bromide 3 (0.43 mmol, 320 mg) and aryl stannane 4 (0.45 mmol, 370 mg) was added tris(dibenzylideneacetone)-dipalladium(0) (0.025 mmol, 24 mg) and tri-o-tolylphosphine (0.1 mmol, 31 mg). The solution was stirred at ambient temperature under $N_2$ for 3 min, brought to 95° C. and reacted overnight. TLC (3% MeOH/$CH_2Cl_2$) of the reaction mixture revealed the removal of some of the THP groups during the reaction. The solution was filtered, the solvent removed by rotary evaporation, and the crude product was reprotected by dissolving in 10 mL of $CH_2Cl_2$, followed by addition of 300 µL of dihydropyran and 10 mg of toluenesulfonic acid monohydrate and stirring for 3 h at ambient temperature. Solvent was removed by rotary evaporation and the residue was purified by flash chromatography on silica eluting with 1:20:79 MeOH/THF/$CH_2Cl_2$ affording 332 mg of biphenyl 4 as a beige oil (58% yield). $^1H$ NMR (400 MHz, $CDCl_3$): δ7.45 (d, 4H, J=2 Hz), 7.29 (t, 2H, J=2 Hz), 4.56–4.63 (m, 12H). MS (ESI): 1338 [M+Na]$^+$.

Example 5

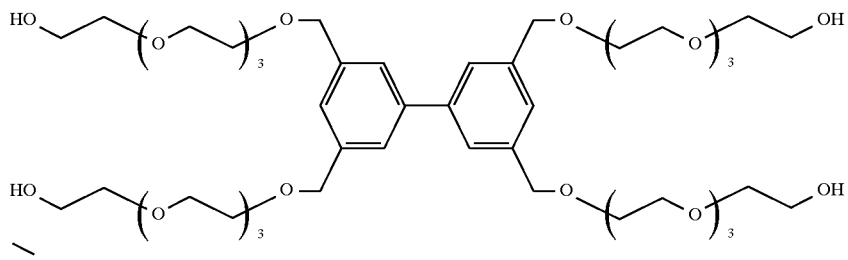

3,5,3',5'-Tetra-(tetraethylene glycoxymethyl) biphenyl

Tetra-THP biphenyl 4 (0.25 mmol, 332 mg) was dissolved in 10 mL of a 0.02M toluenesulfonic acid solution in MeOH and stirred for 2.5 h at room temperature. Removal of the solvent by rotary evaporation, followed by flash chromatography on silica eluting first with 10% MeOH/$CH_2Cl_2$, then 15% MeOH/$CH_2Cl_2$, afforded 210 mg of tetra-ol 6 as a clear oil (85% yield). $^1H$ NMR (400 MHz, $CDCl_3$): δ7.47 (s, 4H), 7.30 (s, 2H), 4.60 (s, 8H).

Example 6

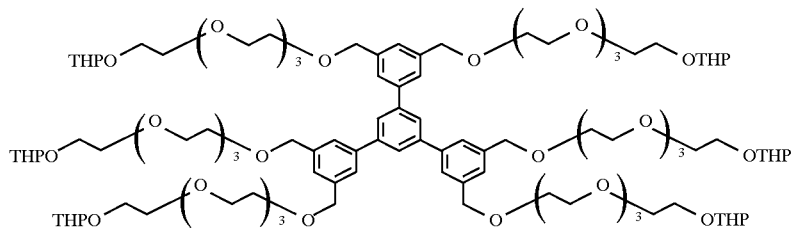

1,3,5-Tris-(3',5'-bis[(tetrahydropyran-2-yl) tetraethylene glycoxymethyl]-phenyl)benzene (5)

To a solution of aryl stannane 4 (0.18 mmol, 150 mg) and 1,3,5-tribromobenzene in 5 mL of dry DMF was added tris(dibenzylideneacetone)-dipalladium(0) (0.0085 mmol, 8 mg) and tri-o-tolylphosphine (0.034 mmol, 10 mg). The solution was stirred under $N_2$ at ambient temperature under for 3 min, brought to 95° C. and heated overnight. As with the biphenyl reaction, TLC (3% MeOH/$CH_2Cl_2$) revealed the removal of some of the THP groups, so the crude reaction mixture was reprotected as described in synthesis of 4. Removal of solvent by rotary evaporation, followed by flash chromatography on silica eluting with 1:20:79 MeOH/THF/$CH_2Cl_2$ afforded 54 mg of 5 as a beige oil (53% yield). $^1$H NMR (400 MHz, $CDCl_3$): δ7.72 (s, 3H), 7.54 (s, 6H), 7.36 (s, 3H), 4.63 (s, 12H), 4.59 (dd, 6H, $J_1$=$J_2$=4 Hz).

Example 7

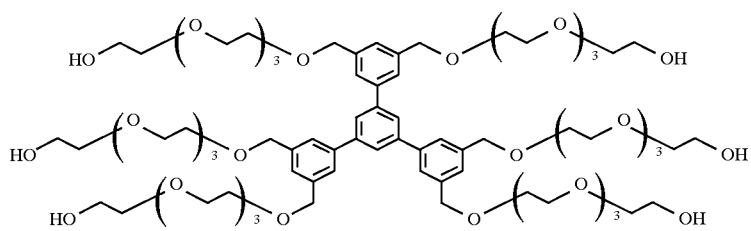

1,3,5-Tris-(3',5'-bis[(tetraethylene glycoxymethyl]-phenyl)benzene (6)

The tetra-THP 5 is deprotected essentially as described in Example 5 with a 0.02M toluenesulfonic acid solution in MeOH at room temperature to give the title compound.

Example 8

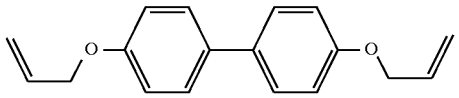

4,4'-Bis-allyloxybiphenyl (7)

Into a 50 ml round bottom flask equipped with magnetic stir bar was added 3.85 g of 4,4'-biphenol (20.7 mmol) and 16.9 g of fine $Cs_2CO_3$ (51.9 mmol). The flask was then purged with nitrogen. Anhydrous DMF (25 ml) was added through the septum. The slurry was sonicated for better mixing before being stirred vigorously for 5 min. Neat ally bromide (4.49 ml, 51.9 mmol) was added to the slurry through the septum. The mixture was vigorously stirred at 40° C. for 24 hours and then quenched with 100 ml of $H_2O$. The mixture was extracted with 3×40 ml of $CH_2Cl_2$. The extractant was dried over $Na_2SO_4$. Evaporation of solvent gave a white solid. This solid was washed with 20 ml of MeOH. Filtration of the slurry gave a colorless crystaline solidine solid (5.49 g 100%). $^1$H NMR ($CDCl_3$) δ7.31 (m, 4H), 6.81 (m, 4H), 5.93 (m, 2H), 5.27 (m, 2H), 5.15 (m, 2H), 4.43 (m, 4H).

Example 9

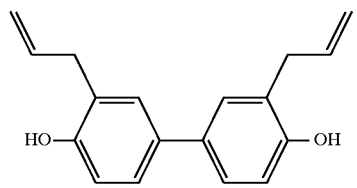

3,3'-Bis-allyl-4,4'-biphenol (8)

Into a 50 ml round bottom flask was added 6.03 g of 7 (22.6 mmol). The flask was purged with $N_2$ and sealed by a septum. The reactant was heated to 190° C. overnight. A light yellow solid was obtained after the reaction was cooled down. This crude product was subjected to a flash column (15% ethyl acetate in hexanes). A white crystaline solid (5.9 g, 97.8%) was obtained. $^1$H NMR (CDCl3) δ7.3-7.25 (m, 4H), 6.83 (m, 2H), 6.04 (m, 2H), 5.22-5.17 (m, 4H), 5.01 (s, 2H), 3.46 (d, 4H).

Example 10

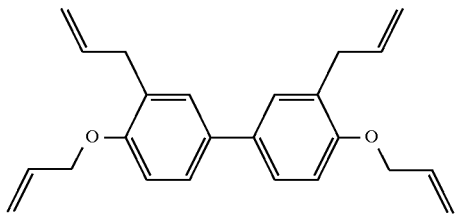

3,3'-Diallyl-4,4'-diallyloxybiphenyl (9)

Into a 50 ml round bottom flask equipped with magnetic stir bar was added 5.9 g of 8 (22.2 mmol) and 13.6 g of fine $K_2CO3$ (98.4 mmol). Anhydrous DMF (25 ml) was added through the septum. The slurry was sonicated for better mixing before being stirred vigorously for 5 min. Neat ally bromide (9.6 ml, 110.8 mmol) was added to the slurry through the septum. The mixture was vigorously stirred at 40° C. for 24 hours before being quenched by 100 ml of $H_2O$. The mixture was extracted with 3×40 ml of $CH_2Cl_2$. The combined extracts were dried over $Na_2SO_4$. Evaporation of solvent gave a white solid, which was washed with 20 ml of MeOH. Filtration of the slurry gave a colorless crystaline solid (6.23 g, 81%). $^1$H NMR ($CDCl_3$) δ7.34-7.30 (m, 4H), 6.85 (m, 2H), 6.04 (m, 4H), 5.43 (m, 2H), 5.26 (m, 2H), 5.12-5.03 (m, 4H), 4.56 (m, 4H), 3.45 (d, 4H).

Example 11

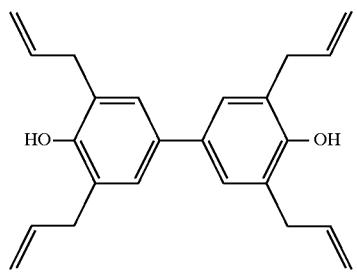

3,3',5,5'-Tetraallyl-4,4'-biphenol (10)

Into a 50 ml round bottom flask was added 5.5 g of 9 (15.9 mmol). The flask was purged with $N_2$ and sealed with a septum. The reactant was heated to 190° C. for 24 hours. The crude product was subjected to a flash column (10% ethyl acetate in hexanes). A white crystaline solid (4.7 g, 85%) was obtained. $^1$H NMR (CDCl$_3$) δ7.16 (s, 4H), 6.02 (m, 4H), 5.19 (s, 2H), 5.16 (m, 8H), 3.43 (d, 8H).

Example 12

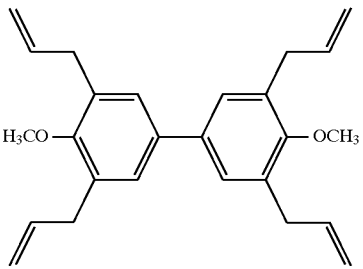

3,3',5,5'-Tetraallyl-4,4'-dimethoxybiphenyl (11)

Into a 50 ml round bottom flask equipped with magnetic stir bar was added 2.5 g of 10 (7.22 mmol), 5.0 g of fine $K_2CO_3$ (36.2 mmol) and 25 ml of DMF. The slurry was sonicated for better mixing before it was stirred vigorously for 5 min. Neat iodomethane (3.6 ml, 57.7 mmol) was added dropwise to the slurry. The mixture was vigorously stirred at room temperature for 24 hours before being quenched by 100 ml of $H_2O$. The mixture was extracted with 3×40 ml of $CH_2Cl_2$. The extract was dried over $Na_2SO_4$. Purification of the crude product by column chromatography (6% ethyl acetate in hexanes) gave a white crystaline solid (2.61 g, 96.5%). $^1$H NMR (CDCl$_3$) δ7.19 (s, 4H), 6.00 (m, 4H), 5.08 (m, 8H), 3.46 (d, 8H).

Example 13

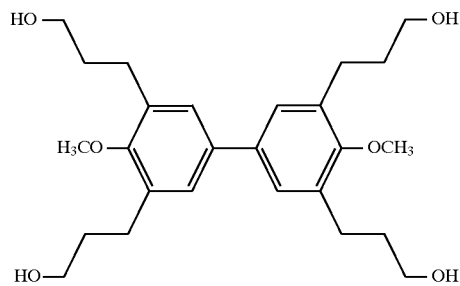

3,3',5,5'-Tetra(3-hydroxypropyl)-4,4'-dimethoxybiphenyl (12)

Into a 250 ml round bottom flask equipped with magnetic stirring bar was added under $N_2$ 1.62 g of 11 (4.3 mmol) in 100 ml of anhydrous THF. A 0.5M solution of 9-BBN in THF (41.3 ml, 20.7 mmol) was added dropwise through- the septum. The reaction mixture was stirred for 3 hour at room temperature. A solution of 25% NaOH (10 g, 100 mmol) was added followed by dropwise addition of 30% $H_2O_2$ (10.0 g, 98 mmol). The reaction mixture was refluxed for 18 hours. After extractive workup by ether, the crude product was purified by flash column chromatography (10% MeOH in $CH_2Cl_2$). A clear oil (1.17 g, 61%) was obtained. $^1$H NMR (CDCl$_3$) δ7.20 (s, 4H), 3.78 (s, 6H), 3.61 (t, 8H), 2.86 (t, 8H), 1.89 (m, 8H).

Example 14

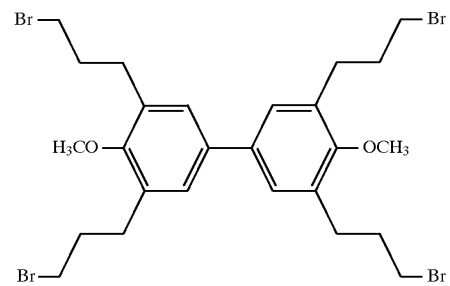

3,3',5,5'-Tetra(3-bromopropyl)-4,4'-dimethoxybiphenyl (13)

Into a 100 ml round bottom flask equipped with magnetic stir bar was added 321 mg of 12 (0.72 mmol), NBS (768 mg, 4.3 mmol), and 25 ml of $CH_2Cl_2$. Triphenylphosphine (1.13 g, 4.3 mmol) was added in small portions into the mixture. The reaction was stopped after 3 hours of stirring by addition of 2 ml of methanol. The solvents were evaporated and a clear oil was obtained. The residue solidified when hexane was added. The solid was triturated and the mixture filtered. The filtrate was evaporated to give a white solid. This crude product was further purified by column chromatography (7.5% ethyl acetate in hexanes). A white crystaline solid (392 mg, 78%) was obtained. $^1$H NMR (CDCl$_3$) δ7.23 (s, 4H), 3.82 (s, 6H), 3.49 (t, 8H), 2.86 (t, 8H), 2.25 (m, 8H); $^{13}$C NMR: δ136.9, 134.3, 127.3, 127.2, 61.5, 33.7, 33.6, 29.0; MS (EI) m/e 698 (M), 618, 602.

Example 15

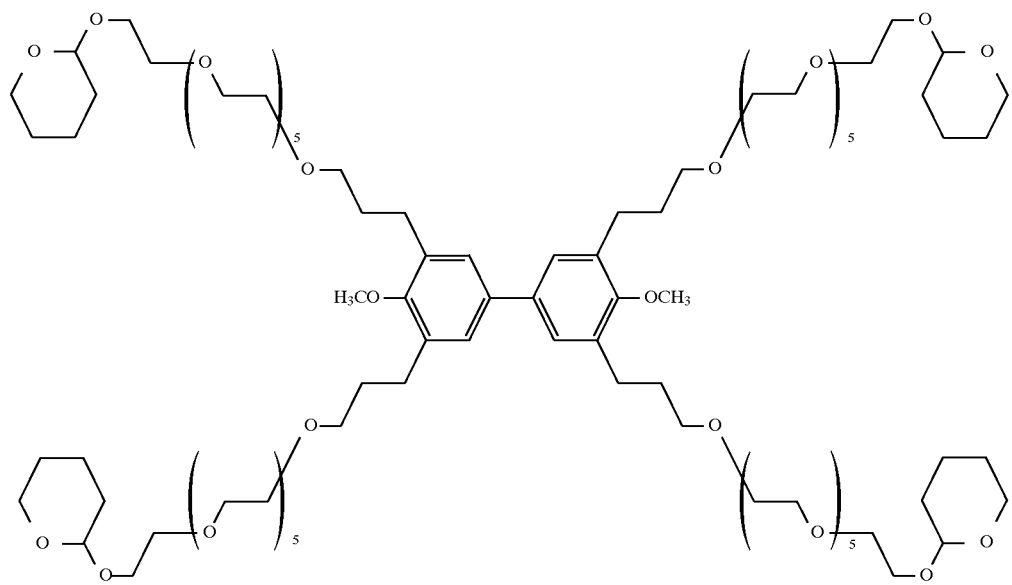

3,3',5,5'-Tetra-[3-(19-tetrahydropyran-2-yl-hexaethylene glycoxy)-propyl]4,4'-dimethoxybiphenyl ether(14)

Into a 10 ml round bottom flask equipped with magnetic stirring bar was added 157.3 mg of 6-PEG-THP (0.43 mmol) in 2 ml of THF, 2 mg of tetrabutylammonium hydrogen sulfate and 1 ml of 50% NaOH. After 5 min of stirring, tetrabromide 13 was added to the mixture. The reaction was allowed to stir at room temperature overnight. After extractive workup with ethyl acetate, the crude product was subjected to a size-exclusion chromatography. The high-molecular weight products were further purified by flash column chromatography (1.5% MeOH, 20% THF in $CH_2Cl_2$). A green oil (22 mg, 16.7%) was obtained. $^1H$ NMR ($CDCl_3$) δ7.20 (s, 4H), 4.64 (t, 4H), 3.87 (m, 8H), 3.77 (s, 6H), 3.66-3.50 (m, 104H), 2.74 (t, 8H), 1.96 (m, 8H), 1.84-1.53 (m, 24H); MS (ESI) m/e 1858.3 ($M·NH_4^+$), 1504, 938, 631.

Example 16

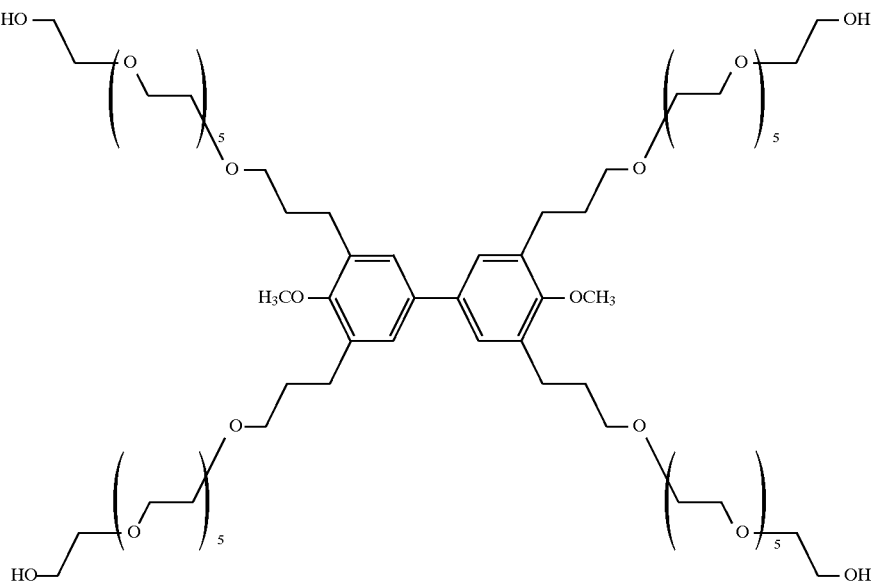

3,3',5,5'-Tetra-[hexa(ethyleneglyoxy)]4,4'-dimethoxybiphenl ether (15)

The tetra-THP 14 is deprotected essentially as described in Example 5 with a 0.02M toluenesulfonic acid solution in MeOH at room temperature to give the title compound.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the Formula I, II or III:

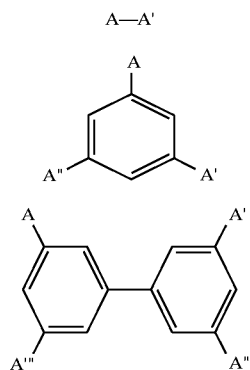

wherein:
A, A', A" and A'" are independently selected from:

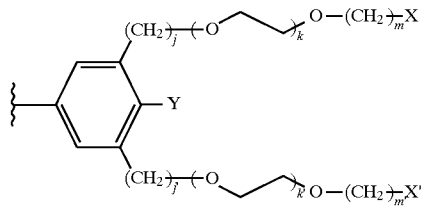

X and X' are independently selected from the group consisting of:
—OH, —Br, —Cl, —I, —SH, —CO$_2$H, —CO$_2$Cl, CO$_2$Br, —SO$_3$H, —SO$_2$Cl, —NH$_2$, and —CH=CH$_2$;
Y is independently selected from the group consisting of:
hydrogen, —CH$_3$, —O—(C$_{1-6}$alkyl) and —O(CH$_2$CH$_2$O)$_n$—CH$_3$;
j and j' are independently an integer from 0 to 4, inclusive;
k and k' are independently an integer from 1 to 12, inclusive;
m and m' are independently an integer from 1 to 4, inclusive; and
n is an integer from 0 to 12, inclusive;
and salts thereof.

2. The compound of claim 1 wherein j and j' are 1, 2 or 3.

3. The compound of claim 2 wherein j and j' are 1 or 3.

4. The compound of claim 1 wherein k and k' are 3 to 7, inclusive.

5. The compound of claim 4 wherein k and k' are 3,4 or 5.

6. The compound of claim 1 wherein m and m' are 2 or 3.

7. The compound of claim 6 wherein m and m' are 2.

8. The compound of claim 1 wherein Y is independently selected from the group consisting of: hydrogen, —CH$_3$, and —OCH$_3$.

9. The compound of claim 1 wherein X and X' are independently selected from the group consisting of: —OH, —Br, —NH$_2$, and —CO$_2$H.

10. The compound of claim 1 wherein Y is independently selected from the group consisting of: hydrogen, and —OCH$_3$.

11. The compound of claim 1 wherein X and X' are —OH.

12. The compound of claim 1 wherein j and j' are 1 or 3, k and k' are 3, 4 or 5, and m and m' are 2.

13. The compound of claim 12 wherein Y is independently selected from the group consisting of: hydrogen, and —OCH$_3$.

14. The compound of claim 12 wherein X and X' are —OH.

15. The compound of claim 1 wherein A, A', A" and A'" (if present in the compound of claim 1) are identical to each other.

16. The compound of claim 1 which additionally comprises a linker functionality which is selected from the group consisting of: 2,4-dimethoxy-4'-hydroxy-benzophenone, 4-(4-hydroxymethyl-3-methoxyphenoxy)-butryic acid, 4-hydroxymethylbenzoic acid, 4-hydroxymethyl-phenoxyacetic acid, 3-(4-hydroxymethylphenoxy)-propionic acid, p-[(R,S)-α-[1-(9H-fluoren-9-yl)methoxyformamido]-2,4-dimethoxy-benzyl1]-phenoxyacetic acid, p-chloromethylphenyl linker, p-hydroxymethylphenyl linker, MBHA linker, HMBA-MBHA linker, Wang linker, Nova Syn TGA linker, Rink acid linker, Rink amide linker, Rink amide MBHA linker, Sieber liker, and trityl linker.

17. A compound which is selected from the group consisting of:

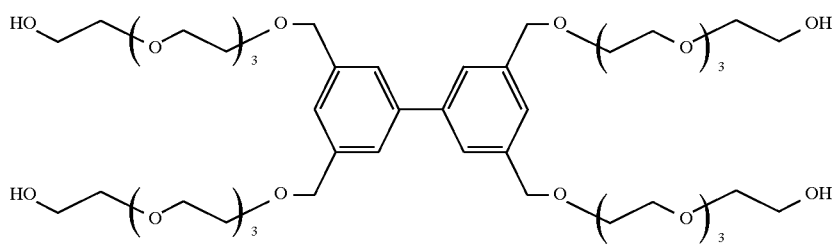

37
-continued
38
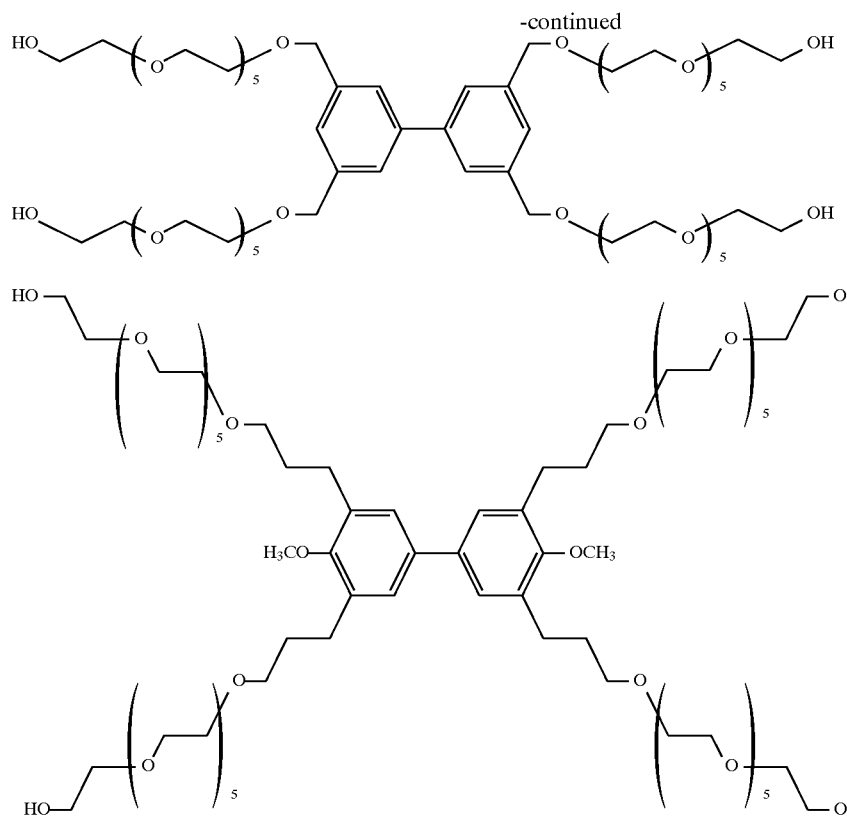
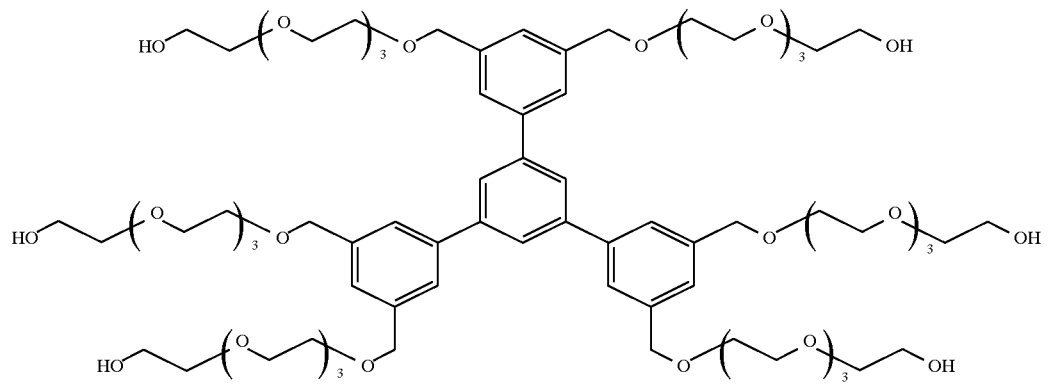
and
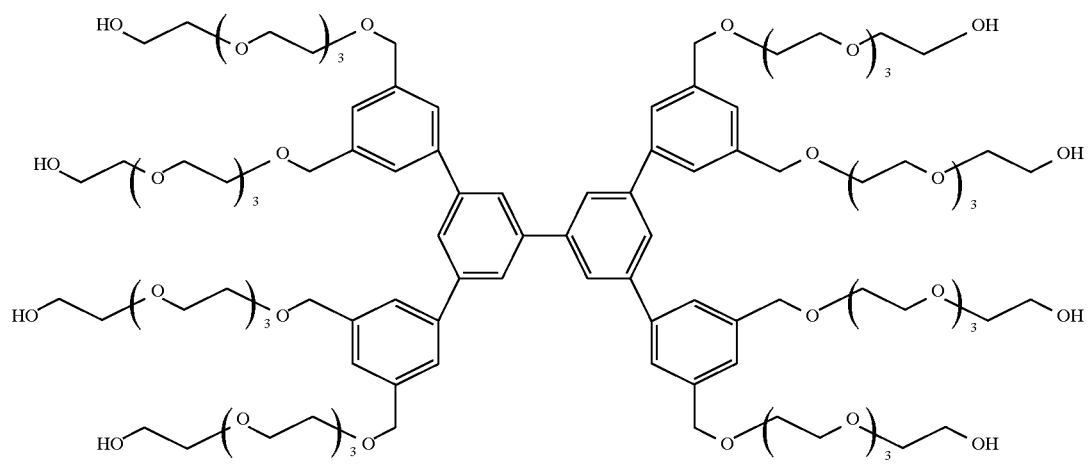

18. A method for using the compound of claim 1 in the preparation of a combinatorial library.

19. A combinatorial library which comprises a plurality of compounds attached to a compound of claim 1.

20. A kit for combinatorial synthesis which comprises a compound of claim 1.

* * * * *